United States Patent
Hartig et al.

(10) Patent No.: US 7,663,766 B2
(45) Date of Patent: Feb. 16, 2010

(54) INCORPORATING FILM OPTICAL PROPERTY MEASUREMENTS INTO SCATTEROMETRY METROLOGY

(75) Inventors: Carsten Hartig, Meerane (DE); Jason P. Cain, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 128 days.

(21) Appl. No.: 11/850,072

(22) Filed: Sep. 5, 2007

(65) Prior Publication Data
US 2009/0059240 A1 Mar. 5, 2009

(51) Int. Cl.
*G01B 11/24* (2006.01)
(52) U.S. Cl. .................................. 356/601; 356/237.2
(58) Field of Classification Search ......... 356/601–604, 356/300, 450, 237.1–237.6, 632, 625, 630, 356/369, 328; 438/16, 401, 695; 430/30, 430/104, 22, 394, 5; 716/4, 7; 451/287, 451/2; 216/84–85; 702/155, 167; 250/559.19, 250/559.2
See application file for complete search history.

(56) References Cited

U.S. PATENT DOCUMENTS

| | | | |
|---|---|---|---|
| 6,259,521 B1 | 7/2001 | Miller et al. | 356/237.5 |
| 6,383,888 B1 | 5/2002 | Stirton | 438/401 |
| 6,451,700 B1 | 9/2002 | Stirton et al. | 438/695 |
| 6,458,605 B1 | 10/2002 | Stirton | 438/7 |
| 6,464,563 B1 | 10/2002 | Lensing | 451/6 |
| 6,479,309 B1 | 11/2002 | Wright | 438/16 |
| 6,524,163 B1 | 2/2003 | Stirton | 451/5 |
| 6,537,833 B1 | 3/2003 | Lensing | 438/14 |
| 6,614,540 B1 | 9/2003 | Stirton | 356/630 |
| 6,630,362 B1 | 10/2003 | Lensing | 438/14 |
| 6,639,663 B1 | 10/2003 | Markle et al. | 356/237.4 |
| 6,650,423 B1 | 11/2003 | Markle et al. | 356/601 |
| 6,657,736 B1 * | 12/2003 | Finarov et al. | 356/625 |
| 6,677,170 B1 | 1/2004 | Markle | 438/16 |
| 6,773,939 B1 | 8/2004 | Wright | 438/16 |
| 6,804,014 B1 | 10/2004 | Markle et al. | 356/625 |
| 6,875,622 B1 | 4/2005 | Markle | 438/14 |
| 6,980,300 B1 | 12/2005 | Lensing et al. | 356/601 |
| 7,262,864 B1 | 8/2007 | Markle et al. | 356/625 |
| 2008/0182343 A1 * | 7/2008 | Deshpande et al. | 438/5 |

* cited by examiner

*Primary Examiner*—Gregory J Toatley, Jr.
*Assistant Examiner*—Tri T Ton
(74) *Attorney, Agent, or Firm*—Williams, Morgan & Amerson, P.C.

(57) ABSTRACT

A method includes collecting optical data from an unpatterned region including a first process layer. At least one optical parameter of the first process layer is determined based on the optical data associated with the unpatterned region. Optical data is collected from a patterned region including a second process layer. At least one characteristic of the patterned region is determined based on the optical data associated with the patterned region and the at least one optical parameter.

20 Claims, 5 Drawing Sheets

INCORPORATING FILM OPTICAL PROPERTY MEASUREMENTS INTO SCATTEROMETRY METROLOGY

CROSS-REFERENCE TO RELATED APPLICATIONS

Not applicable.

STATEMENT REGARDING FEDERALLY SPONSORED RESEARCH OR DEVELOPMENT

Not applicable

BACKGROUND OF THE INVENTION

The disclosed subject matter relates generally to manufacturing and, more particularly, to incorporating film optical property measurements into scatterometry metrology.

There is a constant drive within the semiconductor industry to increase the quality, reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, i.e., local site and worldwide monitoring. These deficiencies can engender non-optimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters.

Semiconductor devices are manufactured from wafers of a substrate material. Layers of materials are added, removed, and/or treated during fabrication to create the electrical circuits that make up the device. The fabrication essentially comprises four basic operations. Although there are only four basic operations, they can be combined in hundreds of different ways, depending upon the particular fabrication process.

The four operations typically used in the manufacture of semiconductor devices are:

layering, or adding thin layers of various materials to a wafer from which a semiconductor device is produced;

patterning, or removing selected portions of added layers;

doping, or placing specific amounts of dopants in the wafer surface through openings in the added layers; and heat treatment, or heating and cooling the materials to produce desired effects in the processed wafer.

The various layers used for forming the features have many specialized functions. Certain layers are used to form conductive features, others perform insulating features, and still others are intermediate layers used to enhance the functionality of the processing steps used to pattern and form the functional layers. In some cases, the ability of a layer to perform its intended function is based mostly on its physical properties, such as its material of construction and thickness, while the ability of other layers to perform their intended function rests on electromagnetic properties, such as refractive index, that may vary based on the particular process used to form the layer.

One technique for measuring characteristics of features of a semiconductor device is optical metrology, such as scatterometry. In scatterometry, a structure, typically including a grid pattern is illuminated with a light source. Measurements of light reflected from the structure are analyzed to determine characteristics of the feature. Generally, variations in the feature result in variations in the reflected light profile.

The accuracy of optical metrology techniques depends, at least in part, on the characterization of the optical properties of the thin films being analyzed (e.g., index of refraction and/or coefficient of extinction). Conventionally, optical properties are characterized outside the measurement domain and assumed to remain constant during subsequent measurements. In some cases, however, manufacturing variations (i.e., intentional or unintentional) can lead to changes in the optical properties of the thin film materials, rusting in a loss of accuracy for the optical measurements.

This section of this document is intended to introduce various aspects of art that may be related to various aspects of the disclosed subject matter described and/or claimed below. This section provides background information to facilitate a better understanding of the various aspects of the disclosed subject matter. It should be understood that the statements in this section of this document are to be read in this light, and not as admissions of prior art. The disclosed subject matter is directed to overcoming, or at least reducing the effects of, one or more of the problems set forth above.

BRIEF SUMMARY OF THE INVENTION

The following presents a simplified summary of the disclosed subject matter in order to provide a basic understanding of some aspects of the disclosed subject matter. This summary is not an exhaustive overview of the disclosed subject matter. It is not intended to identify key or critical elements of the disclosed subject matter or to delineate the scope of the disclosed subject matter. Its sole purpose is to present some concepts in a simplified form as a prelude to the more detailed description that is discussed later.

One aspect of the disclosed subject matter is seen in a method that includes collecting optical data from an unpatterned region including a first process layer. At least one optical parameter of the first process layer is determined based on the optical data associated with the unpatterned region. Optical data is collected from a patterned region including a second process layer. At least one characteristic of the patterned region is determined based on the optical data associated with the patterned region and the at least one optical parameter.

Another aspect of the disclosed subject matter is seen in a system including an optical metrology tool, a process tool, and a controller. The optical metrology tool is operable to collect optical data from an unpatterned region including a first process layer, determine at least one optical parameter of the first process layer based on the optical data associated with the unpatterned region, collect optical data from a patterned region including a second process layer, and determine at least one characteristic of the patterned region based on the optical data associated with the patterned region and the at least one optical parameter. The process tool is operable to process a substrate including at least one of the first process layer or the second process layer in accordance with an operating recipe. The controller is operable to determine at least one parameter of the operating recipe based on the at least one characteristic of the patterned region.

BRIEF DESCRIPTION OF THE SEVERAL VIEWS OF THE DRAWINGS

The disclosed subject matter will hereafter be described with reference to the accompanying drawings, wherein like reference numerals denote like elements, and.

While the disclosed subject matter is susceptible to various modifications and alternative forms, specific embodiments thereof have been shown by way of example in the drawings and are herein described in detail. It should be understood, however, that the description herein of specific embodiments is not intended to limit the disclosed subject matter to the particular forms disclosed, but on the contrary, the intention is to cover all modifications, equivalents, and alternatives falling within the spirit and scope of the disclosed subject matter as defined by the appended claims.

DETAILED DESCRIPTION OF THE INVENTION

One or more specific embodiments of the disclosed subject matter will be described below. It is specifically intended that the disclosed subject matter not be limited to the embodiments and illustrations contained herein, but include modified forms of those embodiments including portions of the embodiments and combinations of elements of different embodiments as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the disclosed subject matter unless explicitly indicated as being "critical" or "essential."

The disclosed subject matter will now be described with reference to the attached figures. Various structures, systems and devices are schematically depicted in the drawings for purposes of explanation only and so as to not obscure the disclosed subject matter with details that are well known to those skilled in the art. Nevertheless, the attached drawings are included to describe and explain illustrative examples of the disclosed subject matter. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Figure 1:
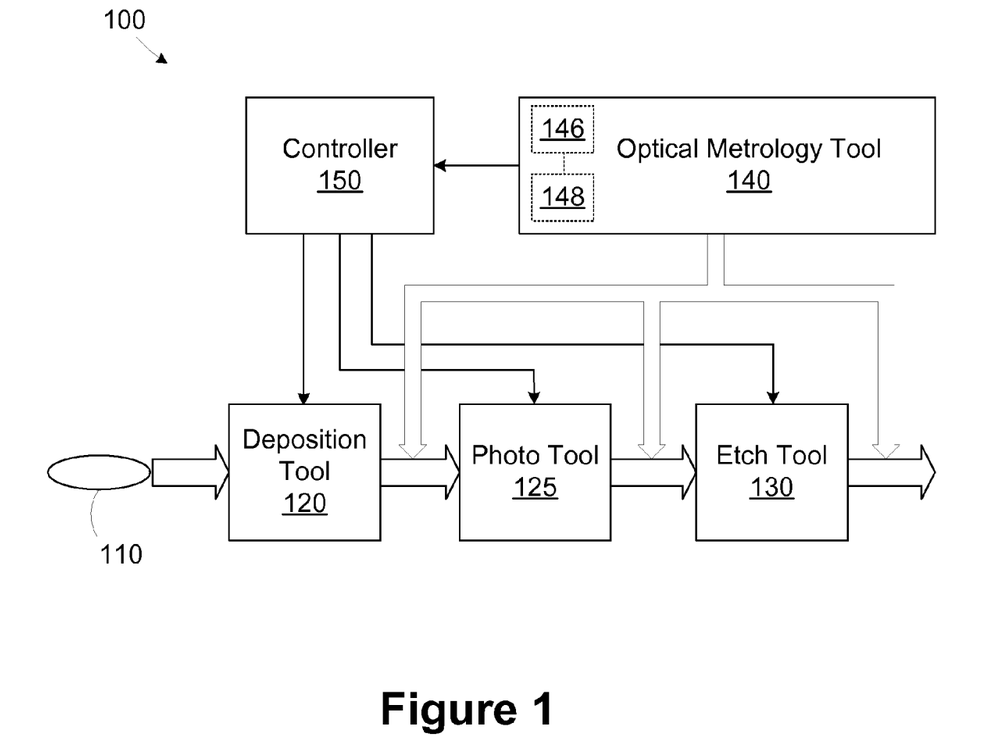
FIG. 1 is a simplified diagram of an illustrative processing line for processing wafers in accordance with one illustrative embodiment of the present invention.

Referring now to the drawings wherein like reference numbers correspond to similar components throughout the several views and, specifically, referring to FIG. 1, the present invention shall be described in the context of an illustrative processing line 100 for processing wafers 110 in accordance with one illustrative embodiment of the present invention is provided. In the illustrated embodiment, the processing line 100 includes a deposition tool 120 for forming one or more process layers on the wafer 110, a photolithography tool 125 for patterning the layers, an etch tool 130 for etching various features in the various process layers, an optical metrology tool 140, and a controller 150.

The deposition tool 120 may be used to form process layers for a semiconductor device, such as polysilicon layers, dielectric layers, metal layers, etc. The photolithography tool 125 may form and pattern layers of photoresist to generate patterns for subsequent etching of the process layers. The etch tool 130 may be employed to form features of the semiconductor device from the process layers. For ease of illustration and to avoid obscuring the present invention, only a portion of the processing line 100 is illustrated. An actual implementation of the processing line 100 may have additional types of tools and multiples instances of each tool type. For example, different etch tools and/or deposition tools may be used to form the process layers or features described above. A particular wafer 110 may be processed multiple times in multiple deposition, photolithography, etch, or other tools to fabricate completed devices thereon. The tools 120, 125, 130 may also comprise cluster tools with multiple chambers or components.

In general, the optical metrology tool 140 may interface with the process line 100 at various points to determine the characteristics of the features formed thereon. In the illustrated embodiment, the optical metrology tool 140 measures an optical property of a film or process layer formed on the wafer 110 and subsequently measures a characteristic of a feature formed on the wafer using the measured optical property. The optical metrology tool 140 includes optical hardware, such as an ellipsometer or reflectometer, and a data processing unit 146 loaded with a scatterometry software application for processing data collected by the optical hardware and comparing the processed data to a reference library 148. For example, the optical hardware may include a model OP5140 or OP5240 with a spectroscopic ellipsometer offered by Therma-Wave, Inc. of Freemont Calif. The data processing unit 146 may comprise a profile application server manufactured by Timbre Technologies, a subsidiary of Tokyo Electron Limited, Inc. of Tokyo, Japan and distributed by Therma-Wave, Inc. The optical metrology tool 140 may be external or, alternatively, the optical metrology tool 140 may be installed in an in-situ arrangement.

The controller 150 provides feedback to one or more of the tools 120, 125, 130 based on the measurements generated by the optical metrology tool 140. The controller 150 adjusts the operating recipe of the controlled tool 120, 125, 130 to improve the deposition and/or etching processes for subsequently processed wafers 110 to affect the characteristics of the features formed (i.e., to reduce variation from target characteristic values).

In the illustrated embodiment, the controller 150 is a computer programmed with software to implement the functions described. However, as will be appreciated by those of ordinary skill in the art, a hardware controller designed to implement the particular functions may also be used. Moreover, the functions performed by the controller 150, as described herein, may be performed by multiple controller devices distributed throughout a system. Additionally, the controller 150 may be a stand-alone controller, it may be integrated into a tool, such as the deposition tool 120, photolithography tool 125, etch tool 130, or the optical metrology tool 140, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Figure 2A:
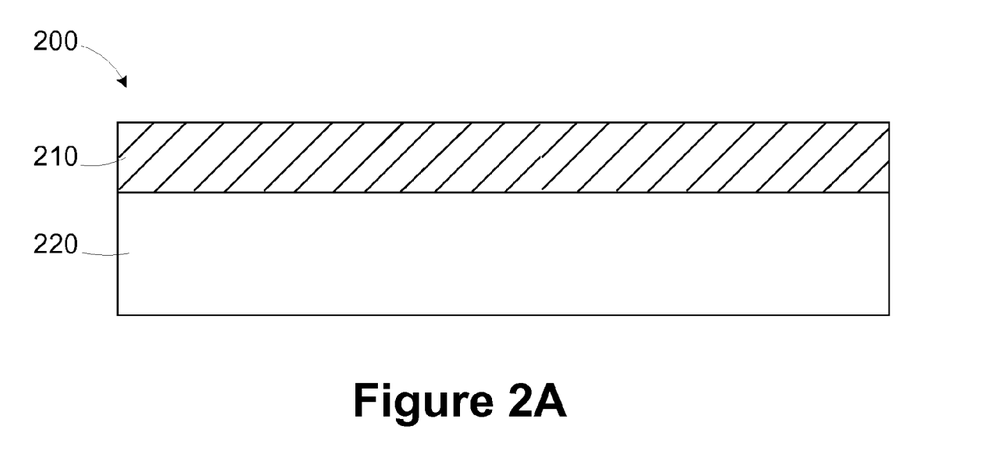
FIGS. 2A and 2B are cross-section views of exemplary semiconductor device structures.
Figure 2B:
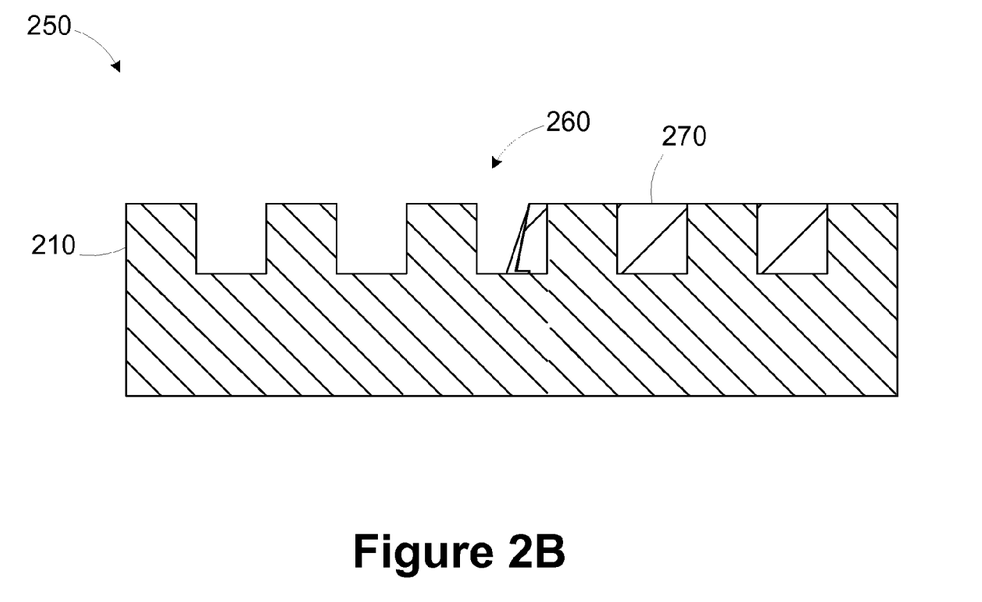

FIGS. 2A and 2B are cross-section views of exemplary structures 200, 250 for use by the optical metrology tool 140 for determining characteristics of a feature formed on the wafer 110. The structure 200 includes a process layer 210 that has substantially no pattern. The process layer 210 may be formed above one or more underlying layers 220. The optical metrology tool 140 measures at least one optical property of the process layer 210, as described in greater detail below.

The structure 250 includes a grid 260 defined at least in part by the process layer 210. For instance the grid 260 may be defined by photoresist lines, polysilicon lines, gate electrodes, trenches, etc. The grid 260 may be periodic in one direction (as shown in FIG. 2) or in multiple directions (e.g., an array of contact holes or vias, a memory cell array). Spaces between grid elements may be filled by a layer 270. The particular material of the process layer 210 and the type of grid 260 formed depend on the point in the process line 100 at which the measurements are taken. For example, if the grid 260 is defined by gate electrodes, the process layer 210 may include polysilicon and may include other layers above or below the polysilicon, such as gate dielectric layers, antireflective coating layers, capping layers, silicide layers, etc. The bottom surfaces between grid elements may be defined by an underlying substrate material. If the grid 260 is defined by trenches, the process layer 210 may be a dielectric layer, and may not extend entirely through the thickness of the process layer 210. The trenches may be unfilled or filled (e.g., with a conductive material, such as copper). For example, trenches may be formed in the layer 220 and filled with the layer 270. The cross-hatching on the layer 210 is different on the structure 250 to indicate that various grid arrangements may be used, as illustrated above. The structure 250 may be a portion of an actual device or a test structure that has material and geometry characteristics similar to those of the actual device.

Figure 3:
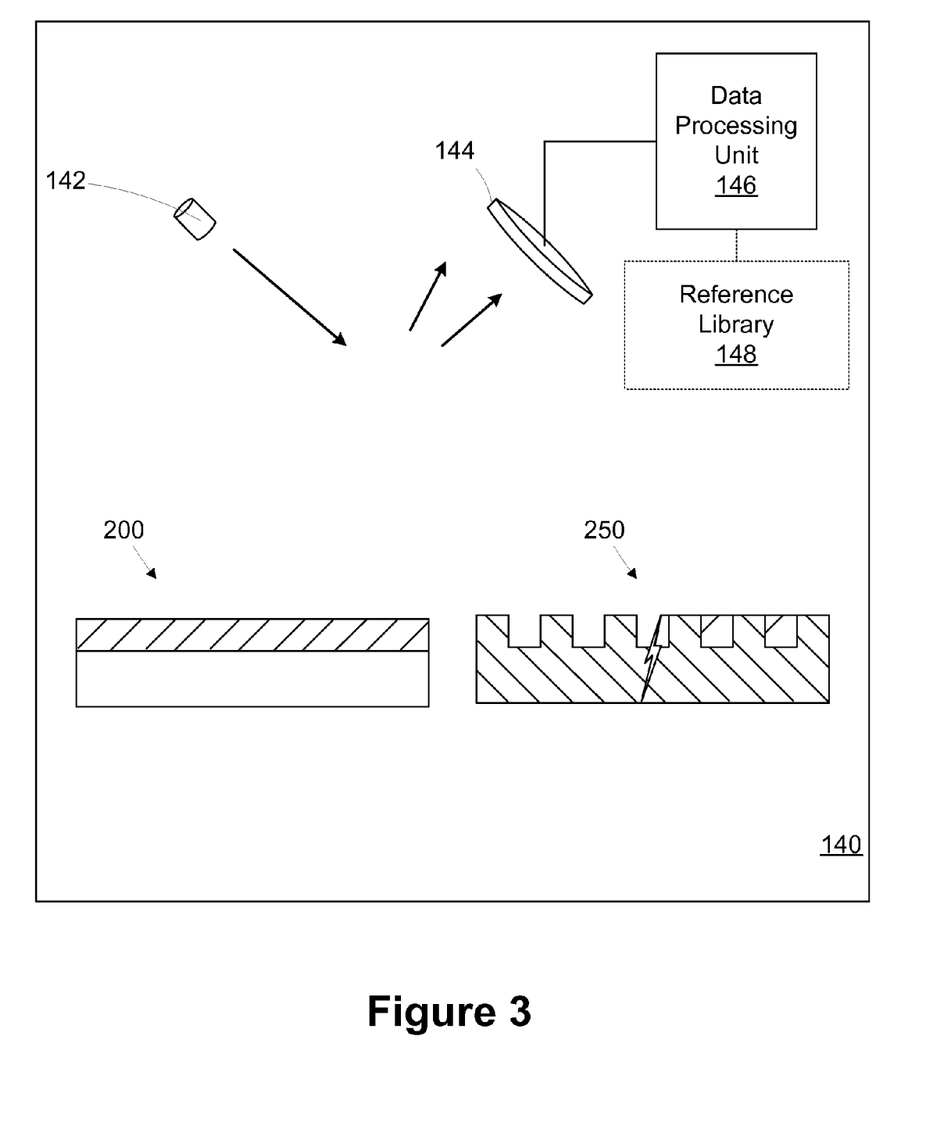
FIG. 3 is a simplified view of the optical metrology tool of FIG. 1 loaded with a substrate.

FIG. 3 is a simplified conceptual view of the optical metrology tool 140 loaded with a wafer or wafers 110 having the structures 200, 250 of FIGS. 2A and 2B. The optical metrology tool 140, includes a light source 142 and a detector 144 positioned proximate one of the structures 200, 250. The light source 142 of the optical metrology tool 140 illuminates at least a portion of one of the structures 200, 250, and the detector 144 takes optical measurements, such as intensity or phase, of the reflected light. A data processing unit 146 receives the optical measurements from the detector 144 and processes the data to identify characteristics of the illuminated structure 200, 250. The reference library 148 may be used to compare measured optical data to previously categorized reference data.

The structures 200, 250 may be formed on the same wafer or on different wafers. For example, the optical metrology tool 140 may measure an optical property of the process layer 210 using the unpatterned structure 200 on a first wafer of a lot and use the measured optical property for measuring characteristics of the grid 260 on the same wafer and on other wafers in the same lot. In other embodiments, the optical metrology tool 140 may perform the optical property measurement on each individual wafer. Moreover, although a single optical metrology tool 140 is illustrated, multiple tools may be provided, one of which measures the optical property using the unpatterned structure 200 and another of which measures a grid characteristic using the structure 250.

The optical metrology tool 140 may use monochromatic light, white light, or some other wavelength or combinations of wavelengths, depending on the specific implementation. The angle of incidence of the light may also vary, depending on the specific implementation. The light analyzed by the optical metrology tool 140 typically includes a reflected component (i.e., incident angle equals reflected angle) and a refracted component (i.e., incident angle does not equal the reflected angle). For purposes of discussion here, the term "reflected" light is meant to encompass both components.

Prior to measuring characteristics of the grid 260, the optical metrology tool 140 collects spectroscopic ellipsometry data from an unpatterned area of the wafer, such as the structure 200. This unpatterned structure 200 need only be large enough to accommodate the spot size of the ellipsometer, typically on the order of 50-100 um square. This ellipsometry data is provided to the data processing unit 146 along with information about the film stack (i.e., film thicknesses and optical properties of all films other than the layer 210 being characterized). The data processing unit 146 selects an appropriate model for the wavelength dependence (dispersion) of the optical properties of the thin film being characterized and fits this model using one or more optimization algorithms. The optimization algorithm varies the film thickness(es) and dispersion model parameters and uses an optical model of the ellipsometer to calculate the simulated ellipsometry response of the film stack including the layer 210. The correct solution set of film thickness(es) and dispersion model parameters is assumed to be the set that minimizes the difference between the simulated and measured ellipsometry data. The data processing unit 146 outputs the fitted optical properties for subsequent scatterometry measurements of the grid 260.

Subsequently, the optical metrology tool 140 uses the measured optical property or properties of the process layer 210 for determining one or more characteristics of the grid 260 defined in the structure 250. Variations in the grid 260 cause changes in the reflection profile (e.g., intensity vs. wavelength—tan($\delta$), phase vs. wavelength—cos($\psi$), where $\delta$ and $\psi$ are common scatterometry outputs known to those of ordinary skill in the art) measured by the optical metrology tool 140 as compared to the light scattering profile that would be present in grids 260 having reference characteristic values.

There are various techniques that may be used to match the current optical data to reference data to characterize the grid 260. In a first embodiment, a plurality of reference profiles may be stored in the reference library 148. The profiles in the reference library 148 may be calculated theoretically by employing Maxwell's equations to model individual spectra based on the expected characteristics of the structure 250. Spectra are generated at a pre-determined resolution for many, if not all, profiles that may be expected, and the sum of all the spectra constitutes the reference library 148. Scatterometry libraries are commercially available from Timbre Technologies, Inc. The profiles in the reference library 148 may also be generated empirically by measuring reflection profiles of sample wafers and subsequently characterizing the measured wafers by destructive or non-destructive examination techniques.

Figure 4A:
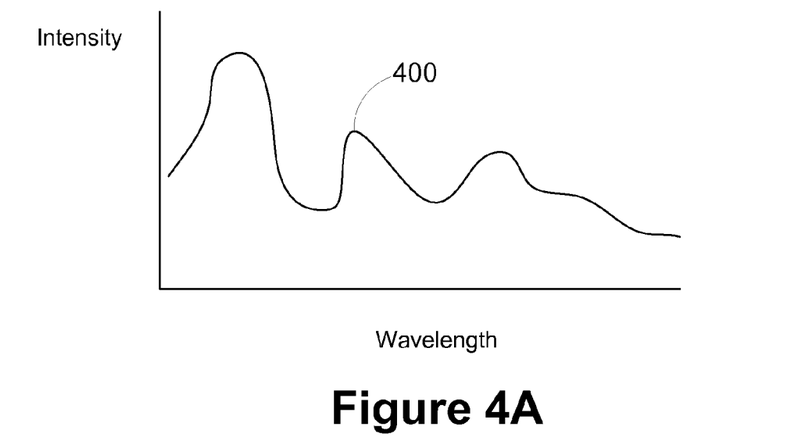
FIGS. 4A, 4B, and 4C illustrate a library of exemplary scatterometry curves used to characterize the grid measured in the optical metrology tool of FIG. 3.
Figure 4B:
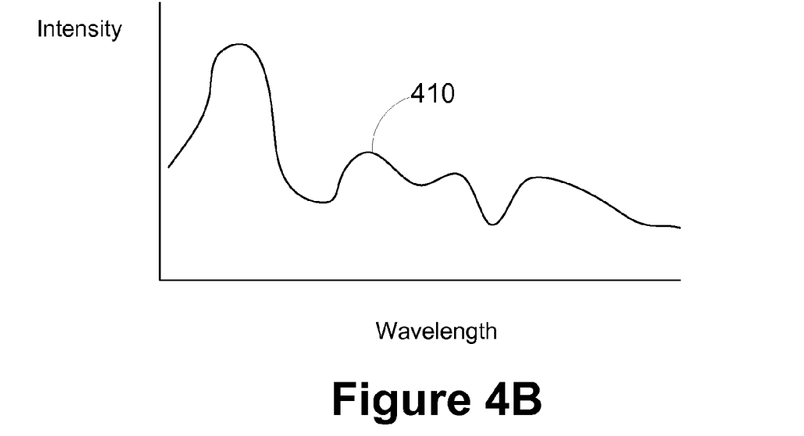
Figure 4C:
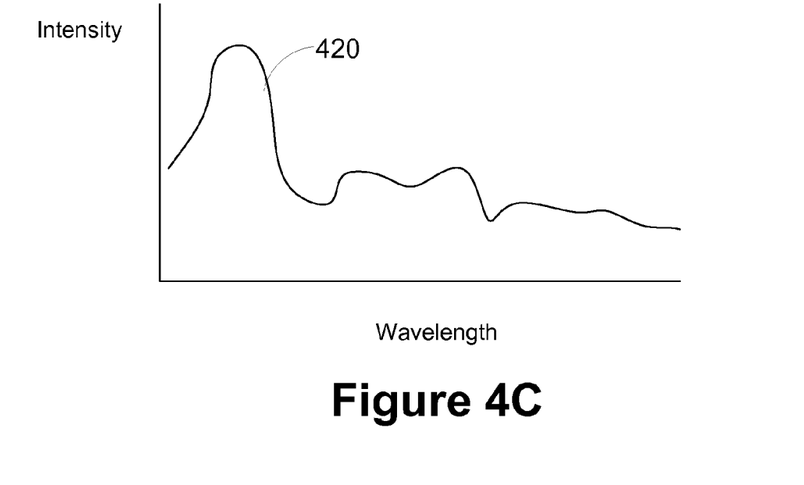

FIGS. 4A, 4B, and 4C illustrate exemplary reflection profiles 400, 410, 420 that may be included in the reference library 148 (see FIGS. 1 and 3) used by the data processing unit 146 to characterize one or more features of the grid 260 (e.g., width, height, pitch, depth, spacing, sidewall angle, fill height, etc.) based on the reflection profiles measured by the optical metrology tool 140. The particular reflection profile expected for any structure 250 depends on the specific geometry and materials of the structure 250 and the parameters of the measurement technique employed by the optical metrology tool 140 (e.g., light bandwidth, angle of incidence, etc.). By incorporating the measured optical properties of the process layer 210 into the data processing, more accurate characterization may be achieved.

Different sets of reference profiles may be generated for different values of optical properties for the process layer. The number of sets and the resolution between sets may be determined based on the degree of variation expected in the index of refraction and/or coefficient of extinction exhibited by the process layer 210, as is measured by the optical metrology tool 140 using the structure 200.

The reflection profile 400 of FIG. 4A represents an exemplary reference profile for a structure 250 where the grid 260 has characteristics corresponding to design or target values. The reflection profile 410 of FIG. 4B represents an exemplary reference profile for a structure 250 where the grid 260 exhibits a pitch slightly larger than a desired target value. The reflection profile 420 of FIG. 4C represents an exemplary reference profile for a structure 250 where the grid 260 exhibits a decreased pitch. The reflection profiles of structures 250 having grids 260 with different amounts pitch variation may be included in the reference library 148. Similarly, reflection profiles may be included that correspond to variations in the depth, width, sidewall profile, etc., of the grid 260. Again, the reference profiles may be grouped into sets indexed by the optical properties of the process layer 210.

The data processing unit 146 receives the measured optical properties of the process layer 210 and a reflection profile measured by the detector 144. The data processing unit 146 then selects a subset of the reference profiles based on the measured optical property or properties of the process layer 210 and compares the measured reflection profile to the subset selected from the reference library 148. Each reference profile has an associated grid characteristic metric related to one or more characteristics of the grid 260. For example, the grid metric may comprise actual width, depth, spacing, fill height, or sidewall profile measurements. The data processing unit 146 determines the reference reflection profile having the closest match to the measured reflection profile. Techniques for matching the measured reflection profile to the closest reference reflection profile are well known to those of ordinary skill in the art, so they are not described in greater detail herein. For example, a least squares error technique may be employed.

In another embodiment, the data processing unit 146 may use a relatively sparse reference library 148 to determine approximate characteristics of the grid 260 and then use a real-time regression model using the approximate characteristics and the measure optical properties of the process layer 210 to generate a more accurate solution that yields grid metrics for the grid 260. The computational requirements of the regression model are reduced in comparison to a full first-principles model due to the rough characterization and the measured optical properties, resulting in a solution that may be used for devices in an actual process flow.

After receiving the grid metric from the optical metrology tool 140, the controller 150 may take a variety of autonomous actions. In one embodiment of the present invention, the controller 150 is adapted to modify the operating recipe of the deposition tool 120, the photolithography tool 125, and/or the etch tool 130 based on the grid characteristic metric to control operations on subsequently processed wafers. The controller 150 may adjust the recipe for subsequently processed wafers to control the characteristics of the grid 260. Deposition parameters (e.g., deposition time, chamber pressure, chamber temperature, reactant gas concentration, etc.), photolithography parameters (e.g., intensity, alignment, wavelength, etc.), or etch recipe parameters (e.g., etch time, plasma chemical compositions, RF power, gas flow, chamber temperature, chamber pressure, end-point signal, etc.) may be changed to correct variations in the width, spacing, depth, fill height, or sidewall profile of the grid 260.

The controller 150 may use a control model of one or more of the tools 120, 125, 130 for determining its associated operating recipe. For example, the controller 150 may use a control model relating the grid characteristic metric to a particular operating recipe parameter in the controlled tool 120, 125, 130 to control the process to correct for variation. This correction may also result in the correction of the process as it affects the other features formed on the device. The control model may be developed empirically using commonly known linear or non-linear techniques. The control model may be a relatively simple equation based model (e.g., linear, exponential, weighted average, etc.) or a more complex model, such as a neural network model, principal component analysis (PCA) model, or a projection to latent structures (PLS) model. The specific implementation of the model may vary depending on the modeling technique selected.

Grid characteristic models may be generated by the controller 150, or alternatively, they may be generated by a different processing resource (not shown) and stored on the controller 150 after being developed. The grid characteristic models may be developed using the tools 120, 125, 130 or using different tools (not shown) having similar operating characteristics. For purposes of illustration, it is assumed that the grid characteristic models are generated and updated by the controller 150 or other processing resource based on the actual performance of the tools 120, 125, 130 as measured by the optical metrology tool 140. The grid characteristic models may be trained based on historical data collected from numerous processing runs of the tools 120, 125, 130.

Figure 5:
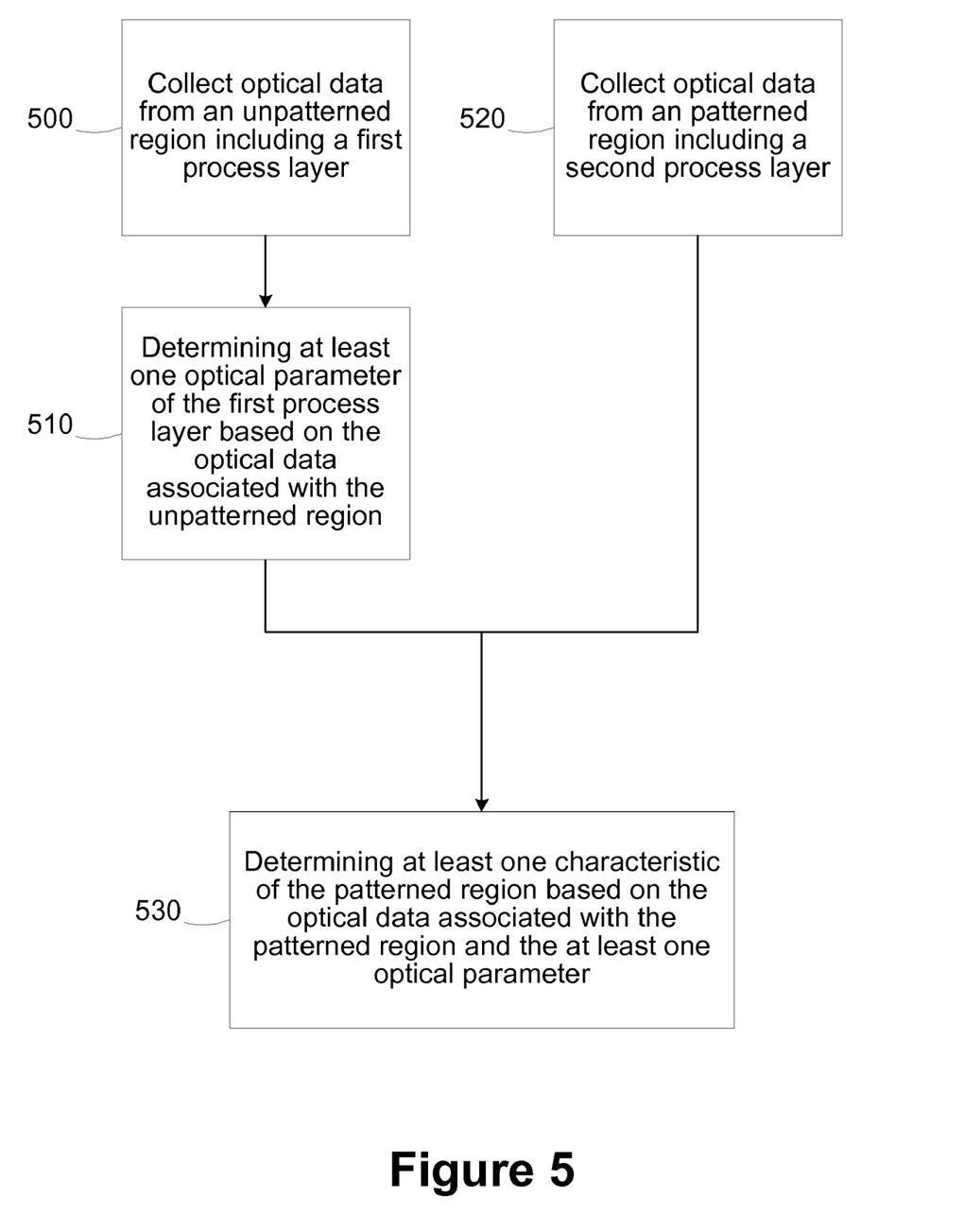
FIG. 5 is a simplified flow diagram of a method for incorporating optical properties of a film into scatterometry measurements in accordance with another illustrative embodiment of the present invention.

FIG. 5 is a simplified flow diagram of a method for determining characteristics of a grid in accordance with another illustrative embodiment of the present invention. In method block 500, optical data is collected from an unpatterned region in which a first process layer is formed. In method block 510, the optical data is processed to extract at least one optical property of the first process layer. In method block 520, optical data is collected from a patterned region including a second process layer. In some embodiments, the first and second process layers may be the same process layer. In method block 530, the optical data collected from the patterned region is analyzed using the at least one optical property to characterize a feature of the patterned region. The collection of optical data from the unpatterned and patterned regions may be conducted sequentially on the same wafer or in parallel on different wafers, such as wafers from the same lot.

The particular embodiments disclosed above are illustrative only, as the disclosed subject matter may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the disclosed subject matter. Accordingly, the protection sought herein is as set forth in the claims below.

We claim:

1. A method, comprising:
    collecting optical data from an unpatterned region including a first process layer;
    determining at least one optical parameter of the first process layer based on the optical data associated with the unpatterned region by:
        modeling a film stack including a plurality of layers, at least one of the layers comprising the first process layer;
        predicting reflection data for the film stack based on a set of properties associated with the film stack;
        comparing the predicted reflection data to the optical data associated with the unpatterned region; and
        iteratively modifying the set of properties, predicting the reflection data, and comparing the predicted reflection data to the optical data associated with the unpatterned region to determine the set of properties yielding the closest matching predicted reflection data;
    collecting optical data from a patterned region including a second process layer; and determining with a processing unit at least one characteristic of the patterned region based on the optical data associated with the patterned region and the at least one optical parameter.

2. The method of claim 1, wherein the at least one optical parameter comprises at least one of an index of refraction or a coefficient of extinction.

3. The method of claim 1, wherein the patterned region comprises a grid structure, and determining the at least one characteristic comprises determining at least one characteristic of the grid structure.

4. The method of claim 3, wherein the characteristic comprises at least one of a width, a height, a pitch, a depth, a spacing, a sidewall angle, or a fill height of the grid structure.

5. The method of claim 3, wherein the grid structure comprises a plurality of lines.

6. The method of claim 3, wherein the grid structure comprises a plurality of trenches.

7. The method of claim 3, wherein the grid structure is periodic in two directions.

8. The method of claim 6, wherein the trenches are filled with a third process layer.

9. The method of claim 1, wherein the first and second process layers comprise the same process layer formed on a common substrate.

10. The method of claim 1, wherein the first and second process layers are formed on first and second different substrates, respectively.

11. The method of claim 10, wherein the first and second substrates comprise first and second wafers grouped into a common lot.

12. The method of claim 1, wherein determining the characteristic of the patterned region further comprises:
    generating a measured reflection profile based on the optical data associated with the patterned region;
    selecting a subset of reference reflection profiles from a reference library based on the at least one optical property, each reference reflection profile having an associated characteristic metric;
    comparing the generated reflection profile to the subset of reference reflection profiles;
    selecting a reference reflection profile from the subset closest to the generated first reflection profile; and
    determining the characteristic of the patterned region based on the characteristic metric associated with the selected reference reflection profile.

13. The method of claim 1, wherein determining the characteristic of the patterned region further comprises:
    generating a measured reflection profile based on the optical data associated with the patterned region;
    comparing the generated reflection profile to a library of reference reflection profiles, each reference reflection profile having at least one associated characteristic metric;
    selecting a reference reflection profile closest to the generated first reflection profile; and
    determining the characteristic of the patterned region using a model that incorporates the at least one optical property and the characteristic metric associated with the selected reference reflection profile.

14. The method of claim 1, further comprising determining at least one parameter of an operating recipe of a tool adapted to process substrates based on the determined characteristic of the patterned region.

15. The method of claim 1, farther comprising generating a reflection profile based on the optical data associated with the patterned region.

16. The method of claim 15, wherein generating the reflection profile comprises generating the reflection profile based on at least one of intensity and phase of light reflected from the patterned region.

17. The method of claim 1, wherein the set of properties includes fixed parameters associated with layers in the film stack other than the first process layer and at least one variable parameter associated with the first process layer.

18. The method of claim 17, wherein the at least one variable parameter comprises at least one of an index of refraction or a coefficient of extinction.

19. A metrology tool, comprising:
a detector operable to collect optical data from an unpatterned region including a first process layer and to collect optical data from a patterned region including a second process layer;
a data processing unit operable to determine at least one optical parameter of the first process layer based on the optical data associated with the unpatterned region and determine at least one characteristic of the patterned region based on the optical data associated with the patterned region and the at least one optical parameter, wherein the data processing unit is operable to determine the at least one optical parameter by modeling a film stack including a plurality of layers, at least one of the layers comprising the first process layer, predicting reflection data for the film stack based on a set of properties associated with the film stack, comparing the predicted reflection data to the optical data associated with the unpatterned region, and iteratively modifying the set of properties, predicting the reflection data, and comparing the predicted reflection data to the optical data associated with the unpatterned region to determine the set of properties yielding the closest matching predicted reflection data.

20. A system, comprising:
an optical metrology tool operable to collect optical data from an unpatterned region including a first process layer, determine at least one optical parameter of the first process layer based on the optical data associated with the unpatterned region, collect optical data from a patterned region including a second process layer, and determine at least one characteristic of the patterned region based on the optical data associated with the patterned region and the at least one optical parameter by modeling a film stack including a plurality of layers, at least one of the layers comprising the first process layer, predicting reflection data for the film stack based on a set of properties associated with the film stack, comparing the predicted reflection data to the optical data associated with the unpatterned region, and iteratively modifying the set of properties, predicting the reflection data, and comparing the predicted reflection data to the optical data associated with the unpatterned region to determine the set of properties yielding the closest matching predicted reflection data;
a process tool operable to process a substrate including at least one of the first process layer or the second process layer in accordance with an operating recipe; and
a controller operable to determine at least one parameter of the operating recipe based on the at least one characteristic of the patterned region.

* * * * *